United States Patent
Cross, Jr.

(10) Patent No.: US 7,781,634 B2
(45) Date of Patent: Aug. 24, 2010

(54) TREATMENT OF OLEFIN FEED TO PARAFFIN ALKYLATION

(75) Inventor: William M. Cross, Jr., Seabrook, TX (US)

(73) Assignee: Catalytic Distillation Technologies, Pasadena, TX (US)

( * ) Notice: Subject to any disclaimer, the term of this patent is extended or adjusted under 35 U.S.C. 154(b) by 727 days.

(21) Appl. No.: 11/650,874

(22) Filed: Jan. 8, 2007

(65) Prior Publication Data
US 2008/0164139 A1    Jul. 10, 2008

(51) Int. Cl.
*C07C 2/58*    (2006.01)

(52) U.S. Cl. .................. 585/717; 585/709; 585/719; 585/721

(58) Field of Classification Search ............ 585/716, 585/700, 709, 717, 719, 721, 723; 208/133, 208/81, 46, 85, 92
See application file for complete search history.

(56) References Cited

U.S. PATENT DOCUMENTS

| | | | |
|---|---|---|---|
| 5,347,061 A | * | 9/1994 | Harandi et al. .............. 585/323 |
| 5,648,586 A | | 7/1997 | Sampath |
| 6,011,191 A | | 1/2000 | Di Girolamo et al. |
| 2004/0077910 A1 | | 4/2004 | Podrebarac et al. |
| 2004/0260136 A1 | * | 12/2004 | Smith et al. ................. 585/730 |

OTHER PUBLICATIONS

PCT International Search Report issued in PCT Application No. PCT/US2007/085406 dated May 9, 2008 (3 pages).
PCT Written Opinion issued in PCT Application No. PCT/US2007/085406 dated May 9, 2008 (4 pages).
Official Action issued in corresponding Ukranian patent application No. A 2009 06744.
Substantaive Examination Adverse Report issued in corresponding Malaysian application No. PI20072019 on Feb. 25, 2010 (4 pages).

* cited by examiner

*Primary Examiner*—Glenn A Caldarola
*Assistant Examiner*—Bradley Etherton
(74) *Attorney, Agent, or Firm*—Osha • Liang LLP

(57) ABSTRACT

A process for the removal of aromatic compounds from an olefin feed to a paraffin alkylation is disclosed. The process may include feeding a olefin and aromatic containing hydrocarbon stream and a dilute alkylate product stream comprising alkylate product and unreacted material from the paraffin alkylation to a distillation zone and removing the unreacted material as overheads and removing a more concentrated alkylate product stream and a portion of the aromatic compounds as bottoms resulting in an improved alkylation process.

3 Claims, 2 Drawing Sheets

TREATMENT OF OLEFIN FEED TO PARAFFIN ALKYLATION

BACKGROUND OF THE INVENTION

1. Field of the Invention

The present invention relates to the alkylation of paraffinic hydrocarbon feed stocks wherein an olefin is reacted with isobutane to produce an alkylate product. More particularly, the invention relates to a process for the preparation of an olefin feed by the removal of aromatic components and an alkylation process related thereto.

2. Related Information

Alkylation is the reaction of a paraffin, usually isoparaffins, with an olefin in the presence of a strong acid which produces paraffins, e.g., of higher octane number than the starting materials and which boil in range of gasolines. In petroleum refining the reaction is generally the reaction of a $C_3$ to $C_5$ olefin with isobutane.

In refining alkylations, hydrofluoric or sulfuric acid catalysts are most widely used. For sulfuric acid catalyzed alkylation low temperature or cold acid processes are favored because side reactions are minimized. In the traditional process the reaction is carried out in a reactor where the hydrocarbon reactants are dispersed into a continuous acid phase. In view of the fact that the cold acid process will continue to be the process of choice, various proposals have been made to improve and enhance the reaction.

As gasoline specifications further limit the quantity of olefins, aromatics and constituent vapor pressure, gasoline will continue to demand lower vapor pressure highly isoparaffinic blend component, such as alkylates. As this occurs, refiners will further convert many of their heavier olefinic streams, such as fluid cracked $C_5$ olefin streams, to meet future gasoline specifications, and they will need a means to efficiently separate aromatic components, such as benzene, toluene and xylenes (BTX) which may be present in theses heavier olefinic feeds. In addition, some $C_4$ olefin feeds, which are produced by dehydrogenation of butanes, may contain aromatic compounds. If not removed, these aromatic contaminants form alkyl sulfonic acids, sometimes referred to as alky sulfonates. Besides causing additional acid consumption, the by-products may cause significant issues with downstream units such as a caustic wash as it will form a stable surfactant (sodium alkyl sulfonate).

SUMMARY OF THE INVENTION

Briefly, the present invention is a process for the removal of aromatic compounds from the olefin feed to an acid paraffin alkylation comprising: feeding an olefin containing hydrocarbon stream and a dilute alkylate product stream from a paraffin alkylation to a distillation zone, removing unreacted material from said hydrocarbon stream as overheads, and removing a more concentrated alkylate product stream and a portion of said aromatic compounds as bottoms.

DETAILED DESCRIPTION OF THE INVENTION

Figure 1:
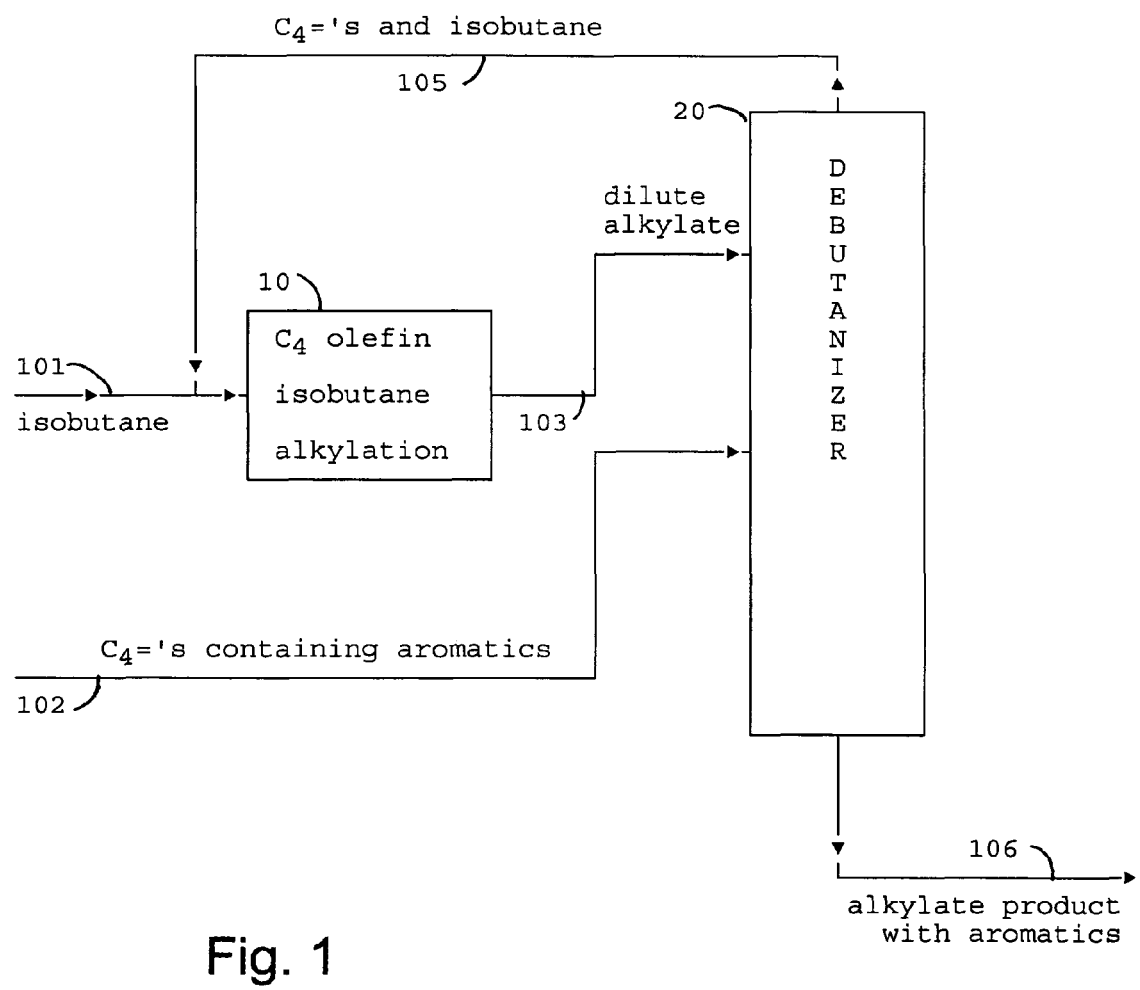
FIG. 1 is a simplified flow diagram of the present invention utilizing $C_4$ olefins.

This invention pertains to the process of removing an aromatic component from an alkylation feed stream, while fractionating a dilute alkylate containing stream. For example, the present invention can be applied for removing BTX from olefins used as alkylation feedstock. As such, the invention provides a means by which sulfuric acid contaminants such as benzene, toluene, and xylene may be removed from an olefin feedstock. It also provides a means for removal of heavier fuel components from olefin containing alkylation feeds, in which the heavier fuel components may be present in the olefin feed or may be produced during the fractionation of the olefin feed.

A conventional fractionation tower is used for the purposes of removing aromatics and separating light isoparaffins, from an alkylate containing stream. The alkylate containing stream, entering this tower as feed, comes from an alkylation unit. The overhead product from this tower goes to an alkylation unit, which may be the same or a different alkylation unit. The fractionation bottoms product is collected and used as blend component for gasoline or further fractionated to produce separated gasoline blend components.

The purpose of the invention is to provide a means to easily separate out heavier components from an olefin feed stream used for alkylation. Typically the prior art, employs two towers for obtaining both an alkylate product and pre-treatment of the olefin feed for alkylation. The present invention provides both functions, using a single tower, and, as such, it provides a lower capital cost investment for incremental alkylation expansions, given that existing equipment is present which can handle the buildup of overhead components, which an alkylation unit cannot convert into $C_5+$ or $C_6+$ type products.

LCN fractionated $C_5$-$C_6$ streams typically contain approximately 0.3 wt. % benzene, which requires removal. The interest in removal of aromatics from feeds resides in the fact that, if they are not removed, these alkylation contaminants cause additional acid spending rates and thus higher operating expense for the refiner. For example, aromatic contaminants, such as benzene, when left in the feed to a sulfuric acid paraffin alkylation form sulfonic acids, sometimes referred to as alky sulfonate (benzene converts to $C_6H_5SO_3H$). The presence of the sulfonic acids downstream of the alkylation unit can cause significant issues with units such as a caustic wash, since it forms a stable surfactant (sodium alkyl sulfonate). For this reason, such aromatics have heretofore been generally removed by setting stringent upstream fractionation requirements. In the present invention this step has been combined with the recovery and concentration of the dilute alkylate from the alkylation.

In the event additional alkylation of the FCC $C_5$ olefins is necessary to reduce the overall RVP in the gasoline pool, dilute alkylation product from an existing $C_4$ alkylation unit, containing a considerable portion of isobutane, can be rerouted from an existing deisobutanizer and used as feed to a depentanizer tower or $C_5$ stripper and a new olefin feed, a $C_5$-$C_6$ LCN cut, can be introduced into a common depentanizer as feed ($C_5$ olefin containing stream). The composite $C_5$ material may be boiled overhead and the resulting overhead stream is sent to an alkylation unit, where the dilute product (overhead) is sent to an existing deisobutanizer and debutanizer. The new $C_5$ feed is BTX free and additional deisobutanizer capacity was not necessary (the BTX having been removed in the bottoms).

The dilute alkylate stream may be fed at a feed point above that where the olefin containing feed stream is introduced or below depending on the feed condition and which of the two feeds requires more liquid traffic to afford removal of the heavy constituent of interest (e.g., BTX).

For the case of the LCN olefin stream, the major $C_5$ olefins may be obtained as part of the overhead stream of the depentanizer, to be used for alkylation feed to a different alkylation unit. It is also desirable to remove the benzene from this feed, which is accomplished by the fractionation step, in which the LCN enters at a top feed location and the dilute alkylate stream enters as a lower feed location of a depentanizer. The bottoms product from this operation is a mixed alkylate and $C_6$ LCN cut.

A $C_4$ dehydrogenation feedstock containing primarily isobutane and isobutylene often contains about 0.3 wt % total aromatics. The aromatics represent a by-product of the dehydrogenation reaction. Removal of these aromatics is essential in reducing acid consumption within the alkylation unit. This feed can both be cleaned of aromatics to produce a good feed for subsequent alkylation (fractionation overhead product) while co-producing a bottoms alkylate product. In this case, a $C_4$ stripper, deisopentanizer, or debutanizer would be used to accomplish this separation.

FIG. 1 illustrates overall alkylation process for the alkylation of isobutane which comprises feeding (1) isobutane and (2) $C_4$ olefins contained in the overheads from a debutanizer to an alkylation reactor wherein isobutane is reacted with $C_4$ olefins to form a dilute alkylate product containing alkylate, which may include isooctane, and unreacted isobutane and trace amounts of $C_4$ olefins; and feeding the dilute alkylate product to a debutanizer; the process is improved according to the present invention by feeding a $C_4$ olefin stream containing aromatic compounds to the debutanizer; removing alkylate product and the aromatic compounds from the debutanizer as bottoms; removing a $C_4$ stream, substantially free of aromatic compounds, from the debutanizer as overheads; and feeding the overheads to the alkylation reactor.

In FIG. 1 the alkylation is for a $iC_4^=$ (isobutylene) steam with isobutane to produce alkylate. As shown, isobutane enters the alkylation via stream 101. The makeup $iC_4^=$'s, containing small amounts of aromatics as describe above, are fed to fractionation column 20, which may be a $C_4$ stripper or deisopentanizer, but which is shown here as a debutanizer via stream 102. Isobutane and isobutylene react in reactor 10 in the presence of concentrated sulfuric acid to form dilute alkylate product which is removed via stream 103 and fed to debutanizer 20, where the $C_4$'s (both unreacted isobutane and isobutylene and the makeup $C_4$'s) are removed as overheads for recycle to reactor 10 via stream 105. The alkylate product, along with any $C_6$ and heavier aromatics, is removed from the debutanizer as bottoms as stream 106. Because the dilute alkylate contains minor amounts of acidic compounds from the reactor, a small portion of the isobutylenes may react with themselves during the fractionation to form dimers, or diisobutylene. This reaction with its by-product is actually helpful in improving the octane of the alkylate blend in the bottoms, since alkylation with isobutylenes does not produce as high an octane alkylate as normal butenes.

If desirable more of the isobutylenes can be dimerized either in the debutanizer (by adding a distillation structure containing a dimerization catalyst) or in a separate dimerization reactor(not shown) in front of the alkylation reactor 10. A typical dimerization catalyst is Amberlyst 15 as manufactured by Rohm and Haas. The use of this catalyst for this purpose in a distillation column type reactor is disclosed in U.S. Pat. No. 4,215,011 which is hereby incorporated by reference. If additional isobutylene is dimerized in the depentanizer the diisobutylene will exit with the bottoms. If a separate upstream dimerization reactor is used, the diisobutylene will be fed to the alkylation reactor 10 and reacted there with isobutane as disclosed in U.S. Pat. No. 6,774,275, which is incorporated herein.

Figure 2:
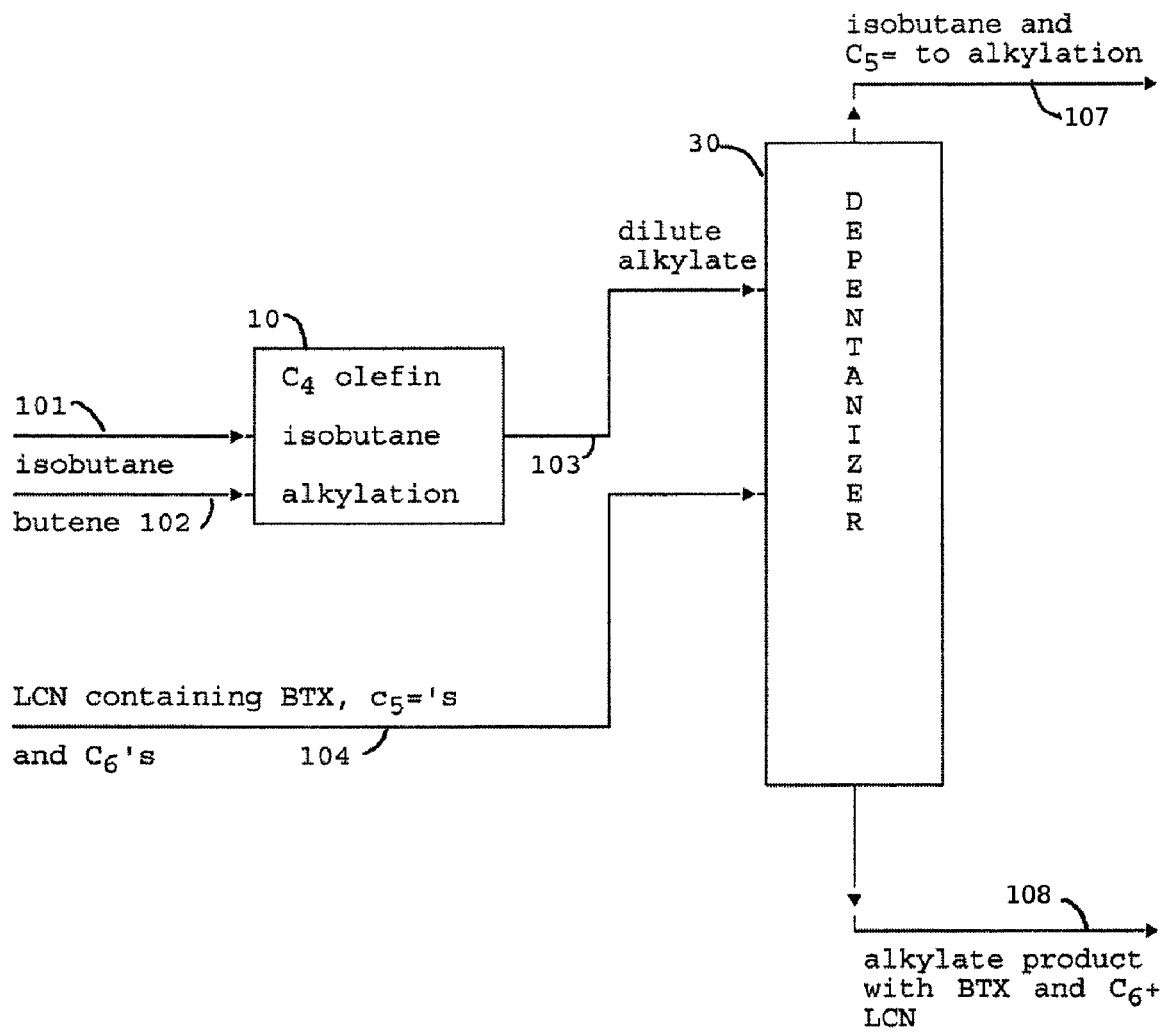
FIG. 2 is a simplified flow diagram of the present invention utilizing $C_5$ olefins from a light cracked naphtha stock.

In some cases the refiner may wish to utilize the $C_5$ olefins contained within a light fluid cracked naphtha (LCN) stream in order to reduce the vapor pressure of the resultant alkylate. As noted above such a stream may contain up to 0.30 wt % aromatics. In this case a two stage alkylation process might be useful, with the first stage reactor using conventional $C_4$ olefins with the unreacted isobutane cascaded to a second stage reactor using the $C_5$ olefins. Such a process is depicted in FIG. 2. The first stage reactor 10 is fed isobutane in stream 101 and $C_4$ olefins (either normal butene or isobutylene) via stream 102. They are reacted together in the reactor 10 in the presence of concentrated sulfuric acid and the effluent from the reactor is sent to a deisobutanizer (not shown) from which a dilute alkylate stream is recovered as bottoms, which is fed to a depentanizer 30 via stream 103. The light cracked naphtha in stream 104 is concurrently fed to the depentanizer where the $C_5$ and lighter material is taken as overheads via stream 107. The $C_6$ and heavier material in the light cracked naphtha, including any aromatics, are taken as bottoms along with the alkylate product in stream 108.

The $C_5$ and lighter overheads contain unreacted isobutane and both may be fed to a second stage alkylation reactor (not shown) wherein the isobutane is reacted with the $C_5$ olefins in the presence of concentrated sulfuric acid to form dilute $C_5$ alkylate (typically a $C_9$ branched alkane). The dilute $C_5$ alkylate, along with any unreacted isobutane is processed through a debutanizer (not shown) with the overheads from the debutanizer being fed to an deisobutanizer (not shown) where the C4's are recovered and recycled to the first reactor 10 or a second stage reactor (not shown).

The invention claimed is:

1. A process for the alkylation of isobutane comprising:
   (a) feeding (1) isobutane and (2) $C_4$ olefins contained in an overheads from a debutanizer to an alkylation reactor wherein isobutane is reacted with $C_4$ olefins to form a dilute alkylate product containing alkylate and unreacted isobutane;
   (b) feeding the dilute alkylate product to the debutanizer;
   (c) feeding a $C_4$ olefin stream containing aromatic compounds to the debutanizer;
   (d) removing a $C_4$ stream substantially free of aromatic compounds from the debutanizer as overheads;
   (e) removing alkylate product and the aromatic compounds from the debutanizer as bottoms; and
   (f) feeding the overheads to the alkylation reactor.

2. The process according to claim 1 wherein said $C_4$ olefin stream contains isobutylene and a portion of said isobutylene is dimerized to diisobutylene in said debutanizer and said diisobutylene is removed in the bottoms with the alkylate product and the aromatic compounds.

3. The process according to claim 1 wherein said $C_4$ olefin stream contains isobutylene and diisobutylene.

* * * * *